United States Patent
Wattiez et al.

(10) Patent No.: US 11,026,981 B2
(45) Date of Patent: Jun. 8, 2021

(54) LDL-CHOLESTEROL-LOWERING CELL EXTRACT AND FOOD SUPPLEMENT

(71) Applicant: ezCol B.V., Rosmalen (NL)

(72) Inventors: Ruddy Wattiez, Sirault (BE); Felice Mastroleo, Vorselaar (BE); Robertus Christiaan Josephus Suters, Rosmalen (NL)

(73) Assignee: ezCol B.V., Rosmalen (NL)

(*) Notice: Subject to any disclaimer, the term of this patent is extended or adjusted under 35 U.S.C. 154(b) by 64 days.

(21) Appl. No.: 16/621,744

(22) PCT Filed: Jun. 14, 2018

(86) PCT No.: PCT/EP2018/065878
§ 371 (c)(1),
(2) Date: Dec. 12, 2019

(87) PCT Pub. No.: WO2018/229223
PCT Pub. Date: Dec. 20, 2018

(65) Prior Publication Data
US 2020/0101120 A1    Apr. 2, 2020

(30) Foreign Application Priority Data

Jun. 15, 2017  (EP) .................... 17176170
Sep. 8, 2017   (EP) .................... 17190079

(51) Int. Cl.
*C12N 1/20*   (2006.01)
*A61K 35/74*  (2015.01)
(Continued)

(52) U.S. Cl.
CPC ............ *A61K 35/74* (2013.01); *A61K 9/0056* (2013.01); *A61K 47/06* (2013.01); *A61P 3/06* (2018.01)

(58) Field of Classification Search
CPC ........................................ C12N 1/20
See application file for complete search history.

(56) References Cited

FOREIGN PATENT DOCUMENTS

| CN | 1172653 | 2/1998 |
|----|---------|--------|
| CN | 1274584 | 11/2000 |

(Continued)

OTHER PUBLICATIONS

Parson et al: 'The biosynthesis of ubiquinone and rhodoquinone from p-hydroxybenzoate and p-hydroxybenzaldehyde in . . . ', Journal of Biological Chemistry 240 (4), p. 1855-1863, May 1965.

(Continued)

*Primary Examiner* — Rosanne Kosson
(74) *Attorney, Agent, or Firm* — N.V. Nederlandsch Octrooibureau; Catherine A. Shultz; Katelyn J. Bernier

(57) ABSTRACT

The present invention relates to a low-density lipoprotein (LDL)-cholesterol-lowering preparation, in particular to a bacterial cell extract for use as a medicament for lowering of the blood plasma LDL-cholesterol level, wherein the extract is obtained by extraction for between 10 minutes and 48 hours at between 8° C. and 37° C., while mixing the cells with the mixture, and wherein the ldl-cholesterol-lowering cell extract and food supplementldl-cholesterol-lowering cell extract and food supplement *Rhodospirillum rubrum* cells are extracted with the mixture in a volume ratio of between 10:1 and 1:10 of petroleum ether with a boiling point of between 60° C. and 80° C. and methanol comprising sodium chloride. More specifically, the present invention relates to a petroleum ether extract of *Rhodospirillum rubrum* obtainable by extraction of *Rhodospirillum rubrum* cells with a mixture of petroleum ether with a boiling point of between 60° C. and 80° C. and methanol comprising sodium chloride. The invention also relates to the petroleum ether extract of *Rhodospirillum rubrum* of the invention, for (Continued)

Figure 1:
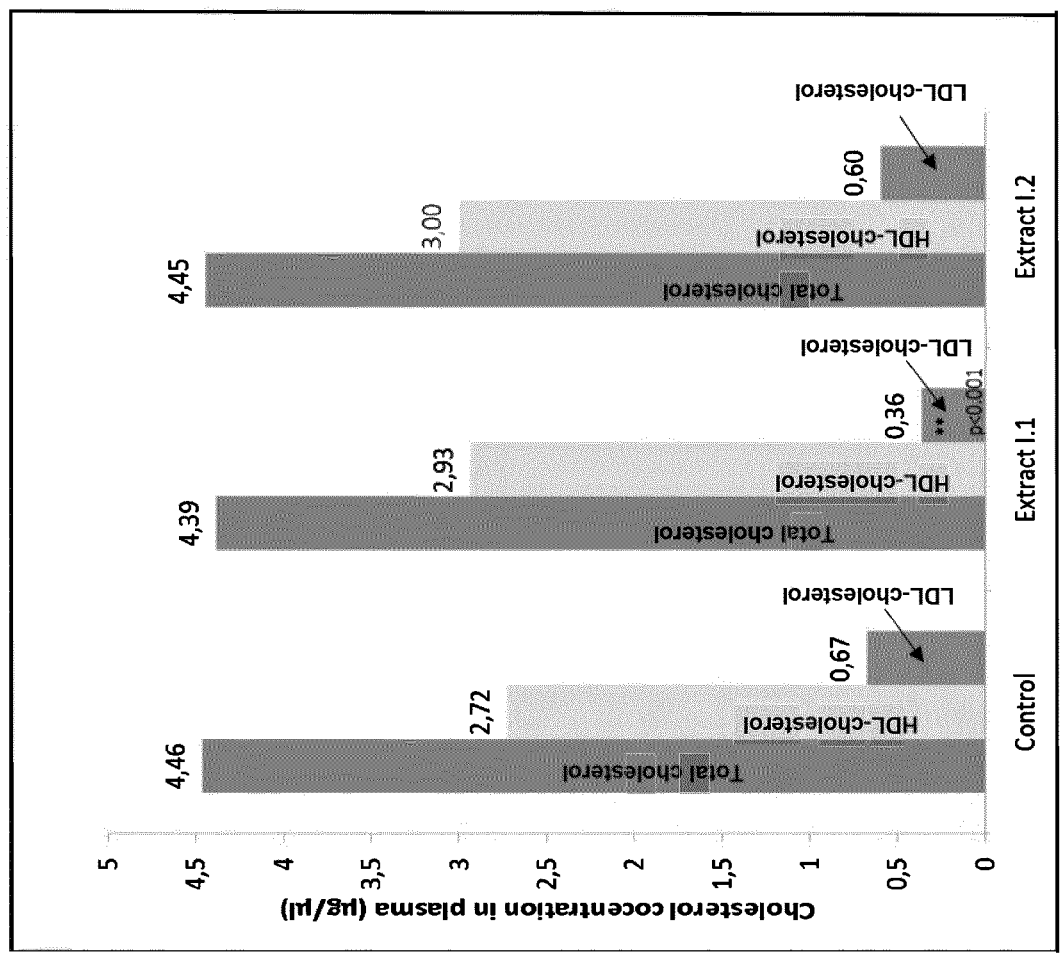

use in a method for the lowering of LDL-cholesterol in blood plasma of a subject. The invention further relates to a pharmaceutical preparation, a food supplement containing said preparation, a foodstuff containing said food supplement, and to a method for their preparation.

17 Claims, 2 Drawing Sheets

(51) Int. Cl.
    *A61P 3/06*     (2006.01)
    *A61K 9/00*     (2006.01)
    *A61K 47/06*    (2006.01)

(56) References Cited

FOREIGN PATENT DOCUMENTS

EP       1569667     9/2005
JP       H08205819   8/1996

OTHER PUBLICATIONS

Minnikin et al: 'An integrated procedure for the extraction of bacterial isoprenoid quinones and polar lipids', Journal of Microbiological Methods 2 (5), p. 233-241, Jul. 1, 1984.

LDL-CHOLESTEROL-LOWERING CELL EXTRACT AND FOOD SUPPLEMENT

TECHNICAL FIELD OF THE INVENTION

The present invention relates to a low-density lipoprotein (LDL)-cholesterol-lowering preparation, in particular to a bacterial cell extract for use as a medicament for lowering of the blood plasma LDL-cholesterol level. More specifically, the present invention relates to a petroleum ether extract of *Rhodospirillum rubrum* obtainable by extraction of *Rhodospirillum rubrum* cells with a mixture of petroleum ether with a boiling point of between 60° C. and 80° C. and methanol comprising sodium chloride. The invention also relates to the petroleum ether extract of *Rhodospirillum rubrum* of the invention, for use in a method for the lowering of LDL-cholesterol in blood plasma of a subject. The invention further relates to a pharmaceutical preparation, a food supplement containing said preparation, a foodstuff containing said food supplement, and to a method for their preparation.

BACKGROUND OF THE INVENTION

Cardiovascular disease is caused by a number of synergistic factors, the most important being a too high blood cholesterol level. Cholesterol is an essential building block for animal and human cells, since it is a component of cell membranes. Human cells can synthesize their own cholesterol, but cholesterol is also assimilated from food. Both processes play an important part in cholesterol metabolism.

Apart from its essential biological role as a building block for cellular membranes, cholesterol also has negative effects on human health, as a cause of cardiovascular disease (such as, for instance, myocardial infarction, stroke, and peripheral vascular disease), more specifically in relation to the occurrence of atherosclerotic lesions in the blood vessel wall. An elevated plasma cholesterol level is the most important predictive risk factor for the occurrence of cardiovascular disease and atherosclerosis.

In blood plasma, cholesterol is transported in so-called lipoproteins, which can be subdivided into a number of different classes, based on their diameter and specific density. The very-low-density lipoproteins (VLDL), the intermediate-density lipoproteins (IDL), the low-density lipoproteins (LDL), and the high-density lipoproteins (HDL) constitute the most important classes of lipoproteins.

Experimental and clinical studies have shown that the amount of cholesterol transported in the VLDL, IDL and LDL classes of lipoproteins (the so-called pro-atherogenic cholesterol) is a risk factor for the occurrence of cardiovascular disease. Cholesterol transported in HDL particles, in contrast, protects against the development of cardiovascular disease (anti-atherogenic cholesterol).

Randomized, placebo-controlled, prospective clinical studies have demonstrated that lowering plasma cholesterol has a favorable effect on the incidence of cardiovascular disease and on mortality. A prerequisite is, though, that the reduction in cholesterol should be predominantly or substantially due to a reduction in the pro-atherogenic cholesterol present in VLDL, IDL and LDL, leaving the level of anti-atherogenic cholesterol preferably essentially unaltered.

For the treatment and prevention of cardiovascular disease it is therefore imperative to reduce the pro-atherogenic cholesterol, and to increase, in absolute or relative proportion, the anti-atherogenic cholesterol.

A number of approaches are available to reduce plasma cholesterol. The most important are:
- to inhibit cholesterol biosynthesis;
- to increase the removal of cholesterol (and/or its metabolites, specifically bile acids) from tissues into the intestinal lumen;
- to reduce the absorption of cholesterol and bile acids from the gastrointestinal tract.

Drugs that are used to inhibit cholesterol synthesis are often inhibitors of the enzyme hydroxymethyl-glutaryl-co-enzyme A reductase (HMGCoA reductase), the rate-limiting enzyme in the cholesterol synthesis pathway. These so-called "statins" are molecules that inhibit enzyme action. Examples are simvastatin, pravastatin and atorvastatin. Statins are generally chemically-synthesized derivatives of naturally-occurring fungal metabolites.

To increase cholesterol removal a bile acid-adsorbing resin can be used (for example cholestyramine). Because of the adsorption of bile acids to the resin, their secretion in the stool is increased, and their reabsorption from the gut into the blood is reduced, resulting in a relative loss of bile acids from the body. Consequently, the liver increases the conversion of cholesterol into bile acids, resulting in a net increase in the secretion of cholesterol (metabolites) from the body. Because bile acids (by solubilizing cholesterol) are essential for the uptake of cholesterol from the lumen into the intestinal tissue, a reduction in bile acid content in the intestinal lumen will also result in a decreased cholesterol uptake.

Drugs that inhibit the active transport of cholesterol from the intestinal lumen to the blood by inhibiting cellular transport systems for cholesterol (and related sterols) in the intestinal epithelial cells are under development.

Cholesterol Homeostasis

Maintenance of cholesterol homeostasis is vital for healthy status and achieved through a regulatory network consisting of genes involved in cholesterol synthesis, absorption, metabolism and elimination. Imbalance of cholesterol level as a results of environmental and genetic factors leads to hypercholesterolemia, a predominant risk factor for atherosclerosis (i.e. hardening of furring of the arteries) and associated coronary and cerebrovascular diseases. Hypercholesterolemia and its associated cardiovascular diseases represent one of the greatest worldwide economic, social and medical challenges that we are facing now.

Despite the wide use of therapeutic drugs for controlling blood cholesterol, like statins inhibiting cholesterol synthesis, the fact remains that it is estimated that more than 50% of the population of the United States has cholesterol levels at the borderline levels (i.e. >2 g/L). In addition, adverse effects associated with therapeutic drugs to control cholesterol levels, such as myopathy, liver damages and potential drug-drug interaction, have been reported. Therefore, development of additional therapies for controlling cholesterol levels is warranted, especially for those with better safety profile.

Chinese patent document CN1274584 discloses a preparation of *Rhodospirillum* for weight-reducing food that reduces blood fat, and a method for the production of said preparation.

Chinese patent document CN1172653 discloses a liquid *Rhodospirillum* preparation for use in the treatment of the human's digestive tract and a method of obtaining said preparation.

Japanese patent document JP08205819 discloses *Rhodospirillum* culture medium and *Rhodospirillum* dried cells for use in a drink or food for use in the treatment of diabetes mellitus, cardiac insufficiency.

None of these documents, however, provides information that a specific part of the cell and/or a specific fraction of the cell obtained upon subjecting the cells to a detailed extraction protocol, would be responsible for the alleged pharmaceutical activity.

Patent EP1569667 discloses a preparation of the membrane fraction of *Rhodospirillum* for use as a medicament, for use in a food supplement, for use in a foodstuff, wherein said use is for lowering plasma cholesterol. Furthermore, EP1569667 discloses a method for providing such membrane fraction of *Rhodospirillum*, said method comprising the steps of: culturing a *Rhodospirillum* cell to a multicellular culture; sonicating said cells; separating the membraneous material from the cytoplasmatic material by centrifugation; further washing and recentrifugation of the pellet retrieved in the previous step.

However, there still exists a need for cholesterol-lowering preparations, specifically for use in the food industry, and preferably aimed at human nutrition.

SUMMARY OF THE INVENTION

An aspect of the present invention relates to a petroleum ether extract of *Rhodospirillum rubrum* by extraction of *Rhodospirillum rubrum* cells with a mixture of petroleum ether with a boiling point of between 60° C. and 80° C. and methanol comprising sodium chloride.

An aspect of the invention relates to a petroleum ether extract of *Rhodospirillum rubrum* obtainable by extraction of *Rhodospirillum rubrum* cells with a mixture of petroleum ether with a boiling point of between 60° C. and 80° C. and methanol comprising sodium chloride, wherein the extract is obtained by extraction for between 10 minutes and 48 hours at between 8° C. and 37° C., while mixing the cells with the mixture, and wherein the *Rhodospirillum rubrum* cells are extracted with the mixture in a volume ratio of between 10:1 and 1:10 of petroleum ether with a boiling point of between 60° C. and 80° C. and methanol comprising sodium chloride.

Preferred is the petroleum ether extract of *Rhodospirillum rubrum* of the invention, wherein the extract is obtained by extraction for between 1 hour and 3 hours at a temperature of between 15° C. and 25° C., while mixing the cells with the mixture, and wherein the *Rhodospirillum rubrum* cells are extracted with the mixture in a 1:1 volume ratio of petroleum ether with a boiling point of between 60° C. and 80° C. and methanol comprising sodium chloride.

An aspect of the present invention relates to the petroleum ether extract of *Rhodospirillum rubrum* according to the invention, for use as a medicament.

An aspect of the present invention relates to the petroleum ether extract of *Rhodospirillum rubrum* according to the invention, for use in the lowering of LDL-cholesterol in blood plasma of a subject.

An aspect of the present invention relates to the petroleum ether extract of *Rhodospirillum rubrum* of the invention, for use in a method for the lowering of LDL-cholesterol in blood plasma of a subject.

An aspect of the present invention relates to the petroleum ether extract of *Rhodospirillum rubrum* according to the invention, for use in the treatment of any of cardiovascular disease, atherosclerosis, dyslipidemia, arteriosclerosis, hypercholesterolemia, familial hypercholesterolemia, hyperlipidemia, an LDL plasma level of at least 70 mg/dL, a total cholesterol level of at least 200 mg/dL, an Lp(a) level of at least 14 mg/dL, inflammation, inflammatory disease, ischemia, infection.

An aspect of the present invention relates to a food supplement with LDL-cholesterol lowering properties, comprising the petroleum ether extract of *Rhodospirillum rubrum* of the invention.

An aspect of the present invention relates to a foodstuff comprising a food supplement of the invention.

An aspect of the present invention relates to a method for the production of a petroleum ether extract of *Rhodospirillum rubrum*, said method comprising the steps of:
  a) providing *Rhodospirillum rubrum* cells and providing biphasic mixture in an about 1:1 volume ratio of petroleum ether with a boiling point of between 60° C. and 80° C. and methanol containing about 0.03% by weight sodium chloride;
  b) mixing the cells of step a) with the mixture of step a) during between about 1 hour and 3 hours, preferably for about 2 hours at between 18° C. and 24° C.; and
  c) isolating the petroleum ether extract of *Rhodospirillum rubrum* from the methanol containing about 0.03% by weight sodium chloride, thereby providing the petroleum ether extract of *Rhodospirillum rubrum*.

SHORT DESCRIPTION OF THE DRAWINGS

FIG. 1 shows the plasma cholesterol lowering effect with regard to LDL-cholesterol in an in vivo animal model. Animals were fed control feed or feed enriched with an extract of *Rhodospirillum rubrum*.

Figure 2:
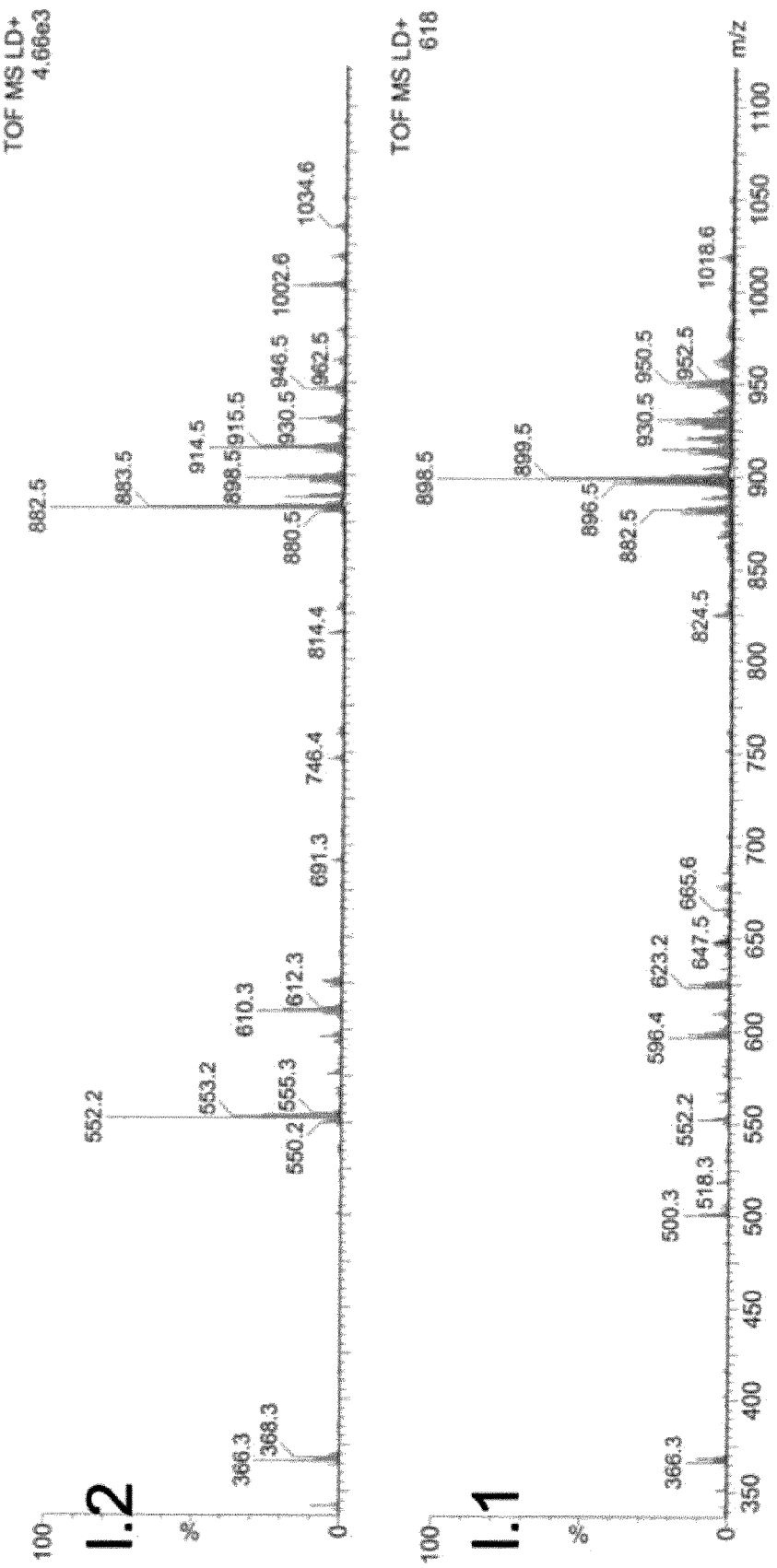

FIG. 2. Maldi TOF analysis of extracts of *Rhodospirillum rubrum*.

DETAILED DESCRIPTION OF THE INVENTION

*Rhodospirillum* is a genus in the family Rhodospirillaceae, a family of purple non-sulphur bacteria of the Order Rhodospirillales and the Class Alpha-proteobacteria. Rhodospirillaceae are, among other characteristics, characterized by being phototrophic, and growing both aerobically and anaerobically, using light as an energy source. To that purpose, the bacteria contain chlorophyll b. Within the genus *Rhodospirillum*, several species are distinguished, e.g. *Rhodospirillum rubrum*, *Rhodospirillum centenum*, *Rhodospirillum photometricum*, *Rhodospirillum oryzae*, *Rhodospirillum sulfurexigens*, *Rhodospirillum salexigens*, *Rhodospirillum salinarum*, *Rhodospirillum sodomense*, and *Rhodospirillum tenue*.

*Rhodospirillum rubrum* is found, among others, in natural waters, in mud, and in sewage treatment plants. The bacterium is used in sewage purification, for biomass production of animal foodstuff (for example as feed for poultry and fish), and as a fertilizer. Biomass of phototrophic bacteria is considered an excellent raw material for animal feed because of its high content of vitamins and amino acids.

The use of *Rhodospirillum rubrum* as animal feed has been practiced for some time. It has been found that *R. rubrum* cells may importantly contribute to the prevention of cardiovascular disease by lowering the cholesterol level in blood plasma and/or blood serum (blood).

A cholesterol-lowering property is herein defined as the capability of a composition, such as a cellular extract, a pharmaceutical composition, a preparation, a food supplement or a foodstuff, when administered to the body of a subject, such as an animal subject, for example a human subject, to lower the cholesterol, or LDL-cholesterol, level of the blood of said subject. Methods for measuring the level of cholesterol in blood are known to the skilled person.

A first aspect of the present invention relates to a petroleum ether extract of *Rhodospirillum rubrum* by extraction of *Rhodospirillum rubrum* cells with a mixture of petroleum ether with a boiling point of between 60° C. and 80° C. and methanol comprising sodium chloride.

A further aspect of the invention relates to a petroleum ether extract of *Rhodospirillum rubrum* obtainable by extraction of *Rhodospirillum rubrum* cells with the mixture of petroleum ether with a boiling point of between 60° C. and 80° C. and methanol comprising sodium chloride, wherein the extract is obtained by extraction for between 10 minutes and 48 hours at between 8° C. and 37° C., while mixing the cells with the mixture, and wherein the *Rhodospirillum rubrum* cells are extracted with the mixture in a volume ratio of between 10:1 and 1:10 of petroleum ether with a boiling point of between 60° C. and 80° C. and methanol comprising sodium chloride.

Throughout the specification the term "petroleum ether with a boiling point of between 60° C. and 80° C." has its regular scientific meaning and here refers to a petroleum fraction consisting of aliphatic hydrocarbons and boiling in the range of between 60° C. and 80° C.

A preparation of *Rhodospirillum* spp. is herein defined as an amount of cellular material of *Rhodospirillum* spp. which has been processed in some way. A preparation of *Rhodospirillum* spp. is, according to the present invention, a petroleum ether extract with cholesterol-lowering properties, such as the petroleum ether extract of *Rhodospirillum rubrum* by extraction of *Rhodospirillum rubrum* cells with a mixture of petroleum ether with a boiling point of between 60° C. and 80° C. and methanol comprising sodium chloride, according to the invention.

A preparation according to the invention consists of a petroleum ether extract derived from one species from the genus *Rhodospirillum*, or a preparation according to the invention consists of a petroleum ether extract derived from mixtures of different *Rhodospirillum* spp. selected for example from *Rhodospirillum rubrum, Rhodospirillum centenum, Rhodospirillum photometricum, Rhodospirillum oryzae, Rhodospirillum sulfurexigens, Rhodospirillum salexigens, Rhodospirillum salinarum, Rhodospirillum sodomense*, and *Rhodospirillum tenue*.

The genus *Phaeospirillum* is a different member of the family of Rhodospirillaceae, which genus comprises *Phaeospirillum fulvum, Phaeospirillum chandramohanii, Phaeospirillum oryzae, Phaeospirillum tilakii* and *Phaeospirillum molischianum*. Therefore, alternatively a preparation according to the invention consists of a petroleum ether extract derived from one species from the genus *Phaeospirillum*, or a preparation according to the invention consists of a petroleum ether extract derived from mixtures of different *Phaeospirillum* spp. selected for example from *Phaeospirillum fulvum, Phaeospirillum chandramohanii, Phaeospirillum oryzae, Phaeospirillum tilakii* and *Phaeospirillum molischianum*.

Of course, a further alternative preparation according to the invention consists of a petroleum ether extract derived from at least one species from the genus *Phaeospirillum* and at least one species from the genus *Rhodospirillum*.

Preferably, a preparation of *Rhodospirillum* spp. and/or of *Phaeospirillum* spp. comprises a petroleum ether extract of *Rhodospirillum rubrum* and/or of *Phaeospirillum molischianum*, still more preferably of the species *Rhodospirillum rubrum* strain ATCC 11170 (strain DSM 467) or strain ATCC 25903 and/or of the *Phaeospirillum molischianum* strain DSM 120 (ATCC, American Type Culture Collection; DSMZ, Deutsche Sammlung von Mikroorganismen and Zellkulturen).

A preparation of *Rhodospirillum* spp. and/or of *Phaeospirillum* spp. according to the invention, may contain 20-100% (w/w), preferably 40-100% (w/w), even more preferably 60-100% (w/w), and optimally 80-100% (w/w) of cellular material from *Rhodospirillum* spp. and/or from *Phaeospirillum* spp., said cellular material being the petroleum ether extract of cells according to the invention. In addition, a preparation may contain other components, depending upon the way the selected preparation is to be prepared. For instance, a preparation may still contain water, or, in the case of a freeze-dried preparation, for example glycerol or sucrose or both.

In a preferred embodiment, a freeze-dried preparation of *Rhodospirillum* spp. and/or of *Phaeospirillum* spp. comprising the petroleum ether extract according to the invention is mixed with filling materials such as microcrystalline cellulose (MCC) or mannitol, with a binder such as hydroxypropyl-cellulose (HPC), and/or lubricants, such as stearic acid and/or other excipients, and pelleted as a dry powder, or prepared for application in a different way.

The petroleum ether extract of *Rhodospirillum rubrum* of the invention is preferably a petroleum ether extract that is obtained by extraction for between 1 hour and 3 hours, preferably for about 2 hours, at between 15° C. and 25° C., preferably at about 18° C. and 24° C., more preferably at about room temperature while mixing the cells with the mixture of petroleum ether with a boiling point of between 60° C. and 80° C. and methanol comprising sodium chloride.

Preferred is the petroleum ether extract of *Rhodospirillum rubrum* according to the invention, wherein the extract is obtained by extraction for between 20 minutes and 24 hours, preferably between 30 minutes and 16 hours, more preferably between 45 minutes and 8 hours, most preferably between 1 hour and 3 hours, at a temperature of between 10° C. and 30° C., preferably between 12° C. and 27° C., more preferably between 15° C. and 25° C., while mixing the cells with the mixture.

In an embodiment of the invention, the petroleum ether extract of *Rhodospirillum rubrum* of the invention is by extraction for about 2 hours at room temperature while mixing the cells with the mixture of petroleum ether with a boiling point of between 60° C. and 80° C. and methanol comprising sodium chloride.

The term "room temperature" as used herein has its conventional meaning and here refers to a temperature of between 20° C. and 22° C.

The petroleum ether extract of *Rhodospirillum rubrum* of the invention is preferably upon centrifugation for between about ten minutes and 60 minutes, preferably for about 20 minutes, at between 18° C. and 24° C., preferably at about 20° C. and 22° C., more preferably at room temperature of the mixture of petroleum ether with a boiling point of between 60° C. and 80° C. and methanol comprising sodium chloride after incubation of *Rhodospirillum rubrum* cells with said mixture.

Preferred is the petroleum ether extract of *Rhodospirillum rubrum* according to the invention, wherein the *Rhodospirillum rubrum* cells are extracted with the mixture of petroleum ether with a boiling point of between 60° C. and 80° C. and methanol containing sodium chloride, in a volume ratio of between 8:1 and 1:8, preferably between 5:1 and 1:5, more preferably between 2:1 and 1:2, most preferably in a 1:1 volume ratio of petroleum ether with a boiling point of between 60° C. and 80° C. and methanol comprising sodium chloride.

Thus, the petroleum ether extract of *Rhodospirillum rubrum* of the invention is preferably by extracting the *Rhodospirillum rubrum* cells with a mixture in an about 1:1 volume ratio, preferably a 1:1 volume ratio of petroleum ether with a boiling point of between 60° C. and 80° C. and methanol containing sodium chloride.

Particularly preferred is the petroleum ether extract of *Rhodospirillum rubrum* of the invention, wherein the extract is obtained by extraction for between 1 hour and 3 hours at a temperature of between 15° C. and 25° C., while mixing the cells with the mixture, and wherein the *Rhodospirillum rubrum* cells are extracted with the mixture in a 1:1 volume ratio of petroleum ether with a boiling point of between 60° C. and 80° C. and methanol comprising sodium chloride.

The petroleum ether extract of *Rhodospirillum rubrum* of the invention is preferably obtained by extracting the *Rhodospirillum rubrum* cells with a mixture of petroleum ether with a boiling point of between 60° C. and 80° C. and methanol comprising about between 0.02% and 0.04% by weight sodium chloride, preferably comprising about 0.03% by weight sodium chloride.

The petroleum ether extract of *Rhodospirillum rubrum* of the invention preferably comprises one or more carotenoids and/or one or more quinones. Preferably, the petroleum ether extract of *Rhodospirillum rubrum* of the invention comprises one or more carotenoids and one or more quinones.

The petroleum ether extract of *Rhodospirillum rubrum* of the invention preferably comprises one or more carotenoids selected from the carotenoids rhodovibrin, 1-hydroxy-spirilloxanthin, 3,4-didehydrorhodopin, chloroxanthin, bacteriopheophytin a, rhodopin, spirilloxanthin, 3,4-dihydrospirilloxanthin and phytyl derivative of bacteriopheophytin a, and/or one or more quinones selected from the quinones ubiquinol-10, ubiquinone-9, ubiquinone-10 and rhodoquinone-10.

The petroleum ether extract of *Rhodospirillum rubrum* of the invention preferably comprises rhodovibrin, 1-hydroxy-spirilloxanthin, 3,4-didehydrorhodopin, chloroxanthin, bacteriopheophytin a, rhodopin, spirilloxanthin, 3,4-dihydrospirilloxanthin, phytyl derivative of bacteriopheophytin a, ubiquinol-10, ubiquinone-9, ubiquinone-10 and rhodoquinone-10.

Without wishing to be bound by theory, Parson & Rudney, in The Journal of Biological Chemistry (Vol. 240, No. 4, April 1965), report on the biosynthesis of ubiquinone and rhodoquinone from p-hydroxybenzoate and n-hydroxybenzaldehyde in *Rhodospirillum rubrum*. Data are presented by these authors which indicate that growing *R. rubrum* catabolizes ubiquinone to the derivative rhodoquinone.

Preferably, the petroleum ether extract of *Rhodospirillum rubrum* of the invention comprises compounds with a molecular weight of at least 2100 Da giving rise to a peak having an m/z value of 752.7 and/or of 769.3 in a nano-electron spray ionization—mass spectrometry (nanoESI-MS) spectrum obtained with, for example, an IonTrap nanoESI-MS high-resolution triple time-of-flight mass spectrometer (Bruker), said one peak or said two peaks with an m/z value of 752.7 and/or of 769.3 having an intensity in the nanoESI-MS spectrum that is at least twice the intensity of the further peaks in the nanoESI-MS spectrum having an m/z value of 665.8 and 883.6, preferably about five times the intensity, according to the invention.

Preferably, the petroleum ether extract of *Rhodospirillum rubrum* of the invention comprises compounds with a molecular weight of at least 2100 Da giving rise to peaks having an m/z value of 752.7 and 769.3 in a nanoESI-MS spectrum obtained with for example an IonTrap nanoESI-MS high-resolution triple time-of-flight mass spectrometer (Bruker), said peaks with an m/z value of 752.7 and 769.3 having an intensity in the nanoESI-MS spectrum that is at least twice the intensity of further peaks in the nanoESI-MS spectrum having an m/z value of 665.8 and 883.6, preferably about five times the intensity, according to the invention.

Preferably, the nanoESI-MS analysis and measurement with the petroleum ether extract of *Rhodospirillum rubrum* of the invention is performed with said petroleum ether extract diluted in 1% v/v formic acid in acetonitrile, according to the invention.

Preferably, the petroleum ether extract of *Rhodospirillum rubrum* of the invention comprises compounds giving rise to one or more peaks, preferably three peaks, of the peaks having an m/z value of 500.3, 882.5 and 898.5 in a matrix-assisted laser desorption ionization time-of-flight (MALDI-ToF) mass spectrometry (MS) spectrum, said one or more peaks with an m/z value of 500.3, 882.5 and 898.5 respectively, having an intensity in the MALDI-ToF MS mass spectra in the ratio of about 1:1:2, preferably about 1:1:3, more preferably about 1:1:4, according to the invention.

Preferably, the petroleum ether extract of *Rhodospirillum rubrum* of the invention comprises compounds giving rise to at least three peaks, said peaks having an m/z value of 500.3, 882.5 and 898.5 respectively in a MALDI-ToF MS spectrum, said three peaks with an m/z value of 500.3, 882.5 and 898.5 respectively, having an intensity in the MALDI-ToF MS mass spectra in the ratio of about 1:1:2, preferably about 1:1:3, more preferably about 1:1:4, according to the invention.

The aforementioned MALDI-ToF MS mass spectra are for example obtained with a Qtof Premier mass spectrometer (Waters) equipped with a Nd:YAG laser, operating at 355 nm with an output frequency of 50 Hz wherein time-of-flight mass analyses are performed in reflection mode at a resolution of about 10.000. Then, the petroleum ether extract of the invention is preferably analyzed using (DCTB)trans-2-[3-(4-tertbutylphenyl)-2-methylprop-2-enylidene] malononitrile matrix.

Preferably, the aforementioned MALDI-ToF MS analysis and measurement with the petroleum ether extract of *Rhodospirillum rubrum* of the invention are performed with said petroleum ether extract dissolved in tetrahydrofuran, according to the invention.

Preferably, the petroleum ether extract of *Rhodospirillum rubrum* of the invention comprises compounds giving rise to at least two peaks, said at least two peaks having an m/z value of 651.6 and 647.6 respectively, in a nanoESI-MS spectrum obtained with for example a triple time-of-flight mass spectrometer (ABSCIEX), said two peaks with an m/z value of 651.6 and 647.6 respectively having an intensity in the nanoESI-MS spectrum with a ratio of about 1:1, preferably about 5:4, more preferably about 2:1, according to the invention.

Preferably, the petroleum ether extract of *Rhodospirillum rubrum* of the invention comprises compounds giving rise to at least two peaks, said at least two peaks having an m/z value of 881.5 and 927.5 respectively, in a nanoESI-MS spectrum obtainable with for example a triple time-of-flight mass spectrometer (ABSCIEX), said two peaks with an m/z value of 881.5 and 927.5 respectively having an intensity in the nanoESI-MS spectrum with a ratio of about 1:1, preferably about 3:2, more preferably about 2:1, according to the invention.

Preferably, the aforementioned nanoESI-MS analysis and measurement with the petroleum ether extract of *Rhodospirillum rubrum* of the invention using an ABSCIEX apparatus are performed with said petroleum ether extract dissolved in a solution consisting of 99% v/v acetonitrile and 1% v/v formic acid, according to the invention.

A further aspect of the present invention relates to the petroleum ether extract of *Rhodospirillum rubrum* according to the invention, for use as a medicament.

An aspect of the present invention relates to the petroleum ether extract of *Rhodospirillum rubrum* according to the invention, for use in the lowering of LDL-cholesterol in blood plasma of a subject.

An aspect of the invention relates to the petroleum ether extract of *Rhodospirillum rubrum* according to the invention, for use in a method for the lowering of LDL-cholesterol in blood plasma of a subject. Similarly, an aspect of the invention relates to the use of the petroleum ether extract of *Rhodospirillum rubrum* according to the invention for the manufacture of a medicament for the treatment of high LDL-cholesterol in blood plasma of a subject. Furthermore, an aspect of the invention relates to the use of the petroleum ether extract of *Rhodospirillum rubrum* according to the invention for the manufacture of a medicament for the lowering of LDL-cholesterol in blood plasma of a subject.

An aspect of the present invention relates to the petroleum ether extract of *Rhodospirillum rubrum* according to the invention, for use in the treatment of any of cardiovascular disease, atherosclerosis, dyslipidemia, arteriosclerosis, hypercholesterolemia, familial hypercholesterolemia, hyperlipidemia, an LDL plasma level of at least 70 mg/dL, a total cholesterol level of at least 200 mg/dL, an Lp(a) level of at least 14 mg/dL, inflammation, inflammatory disease, ischemia, infection.

In an embodiment of the invention, the use of the petroleum ether extract of *Rhodospirillum rubrum* of the invention in the treatment of any of cardiovascular disease, atherosclerosis, dyslipidemia, arteriosclerosis, hypercholesterolemia, familial hypercholesterolemia, hyperlipidemia, an LDL plasma level of at least 70 mg/dL, a total cholesterol level of at least 200 mg/dL, an Lp(a) level of at least 14 mg/dL, inflammation, inflammatory disease, ischemia, infection, is for lowering of LDL-cholesterol in blood plasma of a subject suffering from or having an increased for any of said aforementioned diseases or health issues.

The aforementioned preparations of *Rhodospirillum* spp. and/or preparations of *Phaeospirillum* spp. are very suitable petroleum ether extracts for use as a medicament or as a pharmaceutical preparation to lower plasma cholesterol levels, preferably in human plasma.

Preferably, a petroleum ether extract of *Rhodospirillum rubrum* according to the invention is for use as a medicament according to the invention, wherein said use is in the lowering of LDL-cholesterol in blood plasma of a subject.

In an embodiment of the invention, the petroleum ether extract of *Rhodospirillum rubrum* is used for the lowering of LDL-cholesterol in blood plasma of a subject, wherein the subject suffers from or has an increased risk for any one or more of cardiovascular disease, atherosclerosis, dyslipidemia, arteriosclerosis, hypercholesterolemia, familial hypercholesterolemia, hyperlipidemia, an LDL plasma level of at least 70 mg/dL, a total cholesterol level of at least 200 mg/dL, an Lp(a) level of at least 14 mg/dL, inflammation, inflammatory disease, ischemia, infection.

The petroleum ether extract of *Rhodospirillum rubrum* of the invention preferably lowers the level of LDL-cholesterol in blood plasma, whereas the level of total cholesterol is essentially unaltered and/or whereas the level of HDL-cholesterol is essentially unaltered, when the petroleum ether extract of *Rhodospirillum rubrum* of the invention is for use in the lowering of LDL-cholesterol in blood plasma of a subject.

Surprisingly, the inventors found that the petroleum ether extract of *Rhodospirillum rubrum* of the invention for use as a medicament or as a pharmaceutical preparation to lower plasma cholesterol levels, lowers LDL-cholesterol in plasma with at least 40%, e.g. for about 46%, whereas at the same time both the level of total cholesterol and the level of HDL-cholesterol are essentially unaltered.

Preferably, the petroleum ether extract of *Rhodospirillum rubrum* of the invention for use as a medicament or as a pharmaceutical preparation to lower plasma cholesterol levels, lowers LDL-cholesterol in plasma with at least 20%, preferably with about 40 to 80%, more preferably with about 50%, whereas at the same time both the level of total cholesterol and the level of HDL-cholesterol are essentially unaltered, according to the invention.

The petroleum ether extract of *Rhodospirillum rubrum* according the invention, for use in the lowering of LDL-cholesterol in blood plasma of a subject according to the invention, is preferably administered orally.

Various embodiments of a preparation comprising a petroleum ether extract of *Rhodospirillum* spp. and/or of *Phaeospirillum* spp. according to the present invention are equally possible. For example, a preparation of the invention can be supplied as a fluid preparation of the invention containing solid components suspended, dispersed or emulsified in an aqueous solution, providing a composition according to the invention. Such a composition of the invention can be used directly as a preparation comprising a petroleum ether extract of *Rhodospirillum* spp. and/or of *Phaeospirillum* spp. according to the invention, or can be processed into a food supplement in an alternative embodiment.

An aspect of the current invention relates to a food supplement with LDL-cholesterol lowering properties, comprising the petroleum ether extract of *Rhodospirillum rubrum* according to the invention.

In the present invention a food supplement is defined as a formulation that is consumed in addition to a normal diet and that contains components that do not occur in a normal diet, or that occur in low amounts or in insufficient amounts, while sufficient or increased consumption of these components is desired. Preferably, a food supplement according to the invention is composed such that it is suitable for human consumption. Consequently, a food supplement as defined in the present invention should preferably have a texture, taste and smell, but also a nutritional value, that makes the supplement suitable for human consumption.

In embodiments of the present invention a food supplement with cholesterol-lowering properties comprises a preparation of *Rhodospirillum* spp. and/or of *Phaeospirillum* spp., said preparation comprising a petroleum ether extract of *Rhodospirillum* spp. and/or of *Phaeospirillum* spp. according to the present invention.

A food supplement according to the invention preferably contains between 0.1% and 99.9% (w/w) of a preparation of *Rhodospirillum* spp. comprising a petroleum ether extract of *Rhodospirillum* spp. Preferably, a food supplement contains between 10% and 90% (w/w), even more preferably between 30% and 75% (w/w), of a preparation of *Rhodospirillum* spp and/or of *Phaeospirillum* spp, according to the invention.

To make a food supplement comprising a preparation of *Rhodospirillum* spp. and/or of *Phaeospirillum* spp. comprising a petroleum ether extract of *Rhodospirillum* spp. and/or of *Phaeospirillum* spp. suitable for consumption, components are preferably added to improve, for instance, texture, taste or smell, according to the invention.

Consequently, a food supplement according to the invention preferably comprises (additional) sources of protein, carbohydrate and fat, and vitamins, minerals, electrolytes, trace elements, and other suitable components, so that the food supplement itself is suitable for use as a nourishing food.

As a source of protein each and every protein that is suitable for use in nutritional formulations, and mixtures of these, are preferably used in a food supplement according to the invention. This type of proteins encompasses for instance animal proteins such as whey proteins, whey protein concentrates, whey powder, egg protein, egg albumin, casein, or milk albumin, and plant proteins such as soy protein, soy meal, or proteins from soy milk. For choosing the source of proteins to be used, the biological value of a protein may constitute an important criterion. Caseinate, including calcium caseinate, but also whey, milk albumin, egg albumin, and total egg proteins, for instance, are proteins with a very high biological value, because they contain a large proportion of essential amino acids.

Suitable carbohydrates to be used in a food supplement according to the invention are, for instance, preferably simple short-chain carbohydrates such as mono- and disaccharides, but also polysaccharides, or a combination of both. A carbohydrate is preferably selected because of its suitable organoleptic properties, according to the invention. Preferably, a complex carbohydrate is suitably used as a food fiber, according to the invention.

A food supplement according to the invention preferably contains, in some embodiments, combinations of both simple and complex carbohydrates. A food supplement according to the invention preferably contains, in some embodiments, a fat selected from all edible oils and edible fats.

Vitamins and minerals are preferably added to a preparation according to the invention, in conformity with the rules of the regulatory health authorities, and preferably encompasses all vitamins and minerals endorsed by the above authorities, for instance vitamin A, B1, B2, B12, C, D, B, and K, and folic acid, niacin, pantothenic acid, and biotin. As minerals for instance iron, zinc, iodine, calcium, magnesium, chromium, and selenium are preferably added to a preparation according to the invention.

Electrolytes such as the ions of sodium, potassium, and chloride, and trace elements and other additives do preferably also form part of a food supplement according to the invention. Such components are, if present, preferably used in the recommended concentrations. Additionally, a food supplement according to the invention preferably contains components improving its texture, colorings and flavorings, aromatic substances, spices, fillers, emulsifiers, stabilizing compounds, preservatives, antioxidants, fibers, and other supplements such as amino acids, choline, lecithin, fatty acids, etc. The choice of such components depends upon formulation, design, and preferences. The amounts of such components that are added are known to the skilled person, while the choice of the amounts to be added are preferably guided by considering the recommended daily amounts (RDA) for children and adults.

Emulsifiers are preferably added to stabilize the final product of the invention. Examples of acceptable emulsifiers are lecithin (e.g., derived from soy or from egg), and/or mono- and di-glycerides, according to the invention. As stabilizers, carob, guar or carrageenan are, for instance, preferably used, according to the invention.

Preservatives are preferably added to increase the shelf life of the product of the invention.

Preferably, preservatives such as sodium sorbate, potassium sorbate, potassium benzoate, sodium benzoate, or calcium disodium EDTA are used in a preparation of the invention.

In addition to the carbohydrates mentioned above, natural or synthetic sweeteners, such as saccharides, cyclamates, aspartame, acesulfame potassium, and/or sorbitol, are preferably added to the food supplement, according to the invention.

The amounts of food supplement of the invention to be consumed are varying in size, and are not necessarily restricted to the dosages mentioned in the dosages advised. The term "food supplement" is not meant to be restricted to a specified weight, or to a specified dose of the food supplement.

The composition of a food supplement according to the invention takes in principle any form that is suitable for human or animal consumption, according to the invention.

In a preferred embodiment of the invention, the food supplement is a dry powder that is suitable to be suspended, dispersed or emulsified in an aqueous solution such as coffee, tea, broth, and fruit juice. To that end, the powder is preferably supplied in a dispenser according to the invention.

In an alternative preferred embodiment of the invention, the food supplement is formulated, starting from dry powder, as a tablet. To this end, preferably the composition of a food supplement according to the invention is suitably supplied with fillers such as microcrystalline cellulose (MCC) and mannitol, binders such as hydroxylpropyl-cellulose (HPC), lubricants such as stearic acid, and other excipients.

A food supplement according to the invention is in one embodiment preferably supplied as a fluid, in which the solid components have been suspended, dispersed or emulsified. Such a composition of the invention is preferably directly mixed into a foodstuff, or is preferably for instance extruded and formatted into granules or other forms.

In an alternative embodiment of the invention, a food supplement is preferably formulated in a solid form, such as a bar, a biscuit, or a roll.

A food supplement of the invention is preferably formulated for oral consumption, preferably in combination with an acceptable carrier such as a capsule, a tablet, a water-miscible powder, or another form acceptable for administration. Alternatively, a food supplement of the invention is preferably processed into a foodstuff, according to the invention.

One aspect of the present invention relates to a foodstuff comprising a food supplement according to the invention.

Other aspects of the present invention relate to ways of producing a preparation, a food supplement, or a foodstuff according to the invention.

A further aspect of the present invention relates to a method for the production of a petroleum ether extract of *Rhodospirillum rubrum* of the invention, said method comprising the steps of:

(a) providing *Rhodospirillum rubrum* cells and providing biphasic mixture in a 1:1 volume ratio of petroleum ether with a boiling point of between 60° C. and 80° C. and methanol containing about 0.03% by weight sodium chloride;

(b) mixing the cells of step a) with the mixture of step a) during between about 1 hour and 3 hours, preferably for about 2 hours at between 18° C. and 24° C., preferably at about 20° C. and 22° C., more preferably at room temperature; and (c) isolating the petroleum ether extract of *Rhodospirillum rubrum* from the methanol containing about 0.03% by weight sodium chloride, thereby providing the petroleum ether extract of *Rhodospirillum rubrum*.

A method for the production of a preparation according to the invention preferably involves the steps necessary for culturing cells of one or more *Rhodospirillum* spp. and/or *Phaeospirillum* spp., to harvest the cells in the said culture, and to process the cells of the said culture into a preparation.

Details of such methods are, among others, described in the examples mentioned below. The skilled person will understand that various alternative methods can be used.

During the culturing of cells of *Rhodospirillum* spp. and/or of *Phaeospirillum* spp. anaerobic and phototrophic conditions are applied. As a carbon source, various organic nutrients are preferably used. Very suitable culture media and growth conditions for cells of *Rhodospirillum* spp. and/or of *Phaeospirillum* spp. are for example "Segers and Verstraete medium" (Segers and. Verstraete, 1983), using lactic acid (about 2.7 gram/L) as a carbon source, at a pH of about 6.8-6.9, and at a temperature of 25-37° C., preferably adapted to the specific requirements of the micro-organism involved, at constant light intensity from for instance strip lighting (light intensity 300 μM quanta·$m^{-2} \cdot s^{-1}$) and anaerobically. Other media suitable for culturing *Rhodospirillum* spp. and/or for culturing *Phaeospirillum* spp. are for example "modified Rhodospirillaceae medium" (DSMZ medium #27, DMSZ GmbH, Braunschweig, Germany), or Cens medium (DSMZ medium #748). The cells are suitable to be cultured to a density of between 0.01 mg/mL and 50 mg/mL, preferably between 1 mg/mL and 5 mg/mL based on the wet weight of the cells.

Cells are equally grown anaerobically at 30° C. in 1 liter flasks containing a medium constituting 3.1 ml/L 60% DL-lactate solution, 3 g/L bacteriological peptone and 3 g/L yeast extract in tap water, the pH of the medium being 6.8, and illuminated with an average photon radiation strength of 50 μM quanta·$m^{-2} \cdot s^{-1}$, using 3 Tungsten lamps of 40 W. After 3 days of growth, the optical density at 660 nm amounted 3.5 (1.2 g/kg dry weight).

Once the cells have reached a suitable cell density, they are processed into a preparation according to the invention using separation from the growth medium or harvesting by, for instance, centrifugation or filtration.

The concentrated cell mass is then used, after further processing, as a preparation according to the invention.

The further steps in the processing of cell material of *Rhodospirillum* spp. and/or of *Phaeospirillum* spp. to obtain a usable preparation comprising the petroleum ether extract of *Rhodospirillum* spp. and/or of *Phaeospirillum* spp. of the invention, involves, for example, a washing step, and also involves further processing of the cells by extraction, and optionally freeze-drying.

Minnikin, O'Donnell et al. have described an integrated procedure for the extraction of bacterial isoprenoid quinones and polar lipids (*Journal of Microbiological Methods* 2 (1984) pp. 233-241). A procedure for the sequential extraction of isoprenoid quinones and polar lipids from bacterial cells is outlined by these authors. Extraction with a biphasic mixture of petroleum ether (b.p. 60-80° C.) and methanolic saline gave an upper phase containing isoprenoid quinones. As examples of the procedure, the isoprenoid quinones of *Bacillus subtilis, Mycobacterium avium, Pseudomonas diminuta* and *Streptomyces griseus* were extracted and analyzed.

An aspect of the invention relates to the petroleum ether extract of *Rhodospirillum rubrum* obtainable by the method of the invention.

A food supplement according to the invention may suitably be used to reduce intestinal cholesterol absorption, thus reducing the cholesterol level of blood plasma.

In another embodiment of the invention, a food supplement of the invention is applied in a foodstuff with cholesterol-lowering properties.

A method to prepare a cholesterol-lowering foodstuff of the invention involves the production of a foodstuff incorporating a food supplement according to the invention. Such a method preferably involves a step in which a foodstuff is first prepared in the normal way, followed by the addition of a preparation of *Rhodospirillum* spp. and/or of *Phaeospirillum* spp. to the prepared foodstuff. Also, it is possible to add a preparation of *Rhodospirillum* spp. and/or of *Phaeospirillum* spp. to the foodstuff during its production.

A foodstuff with cholesterol-lowering properties according to the invention contains typically between 0.1% and 20% (w/w), preferably between 1% and 10% (w/w), of the food supplement according to the invention and described above.

The present invention involves finally a preparation of *Rhodospirillum* spp. and/or of *Phaeospirillum* spp. comprising a petroleum ether extract of *Rhodospirillum* spp. and/or of *Phaeospirillum* spp. to be used in a medicament to lower the cholesterol level of blood plasma, preferably to lower the blood plasma level of LDL-cholesterol, while leaving the total cholesterol level in blood plasma essentially unaltered and/or while leaving the HDL-cholesterol level in blood plasma essentially unaltered. Preferably, such a preparation of the invention comprising a petroleum ether extract of *Rhodospirillum* spp. and/or of *Phaeospirillum* spp. involves the species *Rhodospirillum rubrum* and/or the species *Phaeospirillum molischianum*.

The invention is further illustrated by the following examples, which should not be interpreted as limiting the present invention in any way.

EXAMPLES

Experimental Procedures

The *Rhodospirillum rubrum* strain S1H was stored in liquid nitrogen in a 10% w/w sucrose-0.85% w/w saline solution. To regrow the strain, the cells were taken out the liquid nitrogen and thawed for 30 minutes at room temperature. Cells were streaked on a sistrom succinate agar plate and a rich Luria Bertani (LB) medium to grow colony forming units. The agar plates were incubated at 30° C. in dark and aerobic conditions for up to 4 days.

After 4 days, 10 single colonies were picked up and transferred to 10 tubes with 2 mL of Sistrom succinate liquid medium and incubated at 30° C. in dark, aerobic and orbital shaking at 150 rpm. After 4-5 days, the cells were grown and reached an $OD_{680}$=0.5-0.6. To check the axenicity of the cultures, the cells were streaked on a Sistrom succinate agar plate and a rich LB medium agar plate and incubated up to 1 week to look for heterotrophic contaminants. When the axenicity check was approved, the 2 mL cultures were transferred to 15 mL of Sistrom succinate liquid medium and incubated at 30° C. in dark, aerobic and orbital shaking at 150 rpm. After 4-5 days the cells were grown and reached an $OD_{680}$=0.5-0.6. Then, the 15 mL cultures were transferred to 100 mL of Sistrom succinate liquid medium and incubated at 30° C. in dark, aerobic and orbital shaking at 100 rpm. After 4-5 days, the cells were grown and reached an $OD_{680}$=0.5-0.6. Once the axenicity was checked on Sistrom succinate and LB medium, these cells constituted the inoculum cultures.

Cell Culturing
Culture Conditions
Bioreactor

Light anaerobic conditions were applied for culturing the *Rhodospirillum rubrum* strain S1H cells. Ten axenic inoculum cultures were pelleted by centrifugation at 5000*g for 10 minutes. The supernatant was discarded and the pellets were pooled in 25 mL of Melissa liquid medium with acetate as carbon source (Segers & Verstraete, 1983) to constitute a concentrated inoculum.

The bioreactor was sterilized by wet-heat sterilization, 20 minutes of water vapor exposure at 121° C. and 1.2 bar in an autoclave. After sterilization the bioreactor was closed. Bottles with Melissa medium, 1 M $H_2SO_4$, and for the effluent were coupled aseptically in a laminar flow cabinet (LAF).

Extraction Protocols 30 g of bacterial pellet of *Rhodospirillum rubrum* strain S1H cells, are mixed using 440 ml of a biphasic mixture of petroleum ether (boiling point 60-80° C.) and methanolic saline during 2 h at room temperature (biphasic mixture: 220 ml containing 20 ml of NaCl 0.3% by mass and 200 ml of methanol+220 ml of the petroleum ether (boiling point 60-80° C.)). After centrifugation at 5000 RPM during 20 minutes at room temperature, the upper phase (the petroleum ether phase) was removed and stored at room temperature. Lower phase (the methanolic saline solution) was optionally submitted to a second extraction with an additional 220 ml of petroleum ether for 2 h at room temperature. The second upper phase was mixed with the first one and dried using a rotavapor system. The resulting viscous liquid was named "FRACTION I.1", or "fI.1", or "Extract I.1" in FIG. 1.

For obtaining an alternative extract of *Rhodospirillum rubrum* strain S1H cells, 260 ml of $CHCl_3/CH_3OH/NaCl$ 0.3% (9:10:3) solution was added to the above mentioned lower phase (methalonic saline solution) and then incubated under agitation during 4 h at room temperature. After removing insoluble bacterial material by filtration, the supernatant was mixed with 145 ml of $CHCl_3$ and 145 ml of NaCl 0.3% and then incubated 1 h under agitation at room temperature. Finally, the resulting organic phase (lower phase) was removed and dried using a rotavapor and named "FRACTION I.2, or fI.2", or "Extract I.2" in FIG. 1.

A third extract, "Extract III", or "FRACTION III", or "fIII", was obtained as follows. Membranes of *Rhodospirillum rubrum* strain S1H cells were isolated from 30 g of bacterial pellet which was washed in 5 mM phosphate buffer, pH 7.0. Washed bacterial pellet was broken by sonication (3 times for 30 sec, 100 amplitude at 4° C.), 1 Freeze-thaw cycle and 2 French Press cycle (Thermo, High pressure cell, 1500 psi) cycle. The bacterial homogenate was centrifuged at 5,000 rpm for 5 min to remove cellular debris, and the supernatant from this first centrifugation step was centrifuged in a second centrifugation step for 30 min at 15,000 rpm to pellet the membranes. Extract III is the supernatant after the second centrifugation step.

Materials and Methods for Mass Spectrometry Analysis
MALDI-ToF

Matrix-assisted laser desorption ionization time-of-flight (MALDI-ToF) mass spectrum was recorded using a QToF Premier mass spectrometer equipped with a Nd:YAG laser, operating at 355 nm with a output frequency of 50 Hz. Time-of-flight mass analyses were performed in reflection mode at a resolution of about 10.000. Samples of fI.1 and fI.2 were analyzed using (DCTB)trans-2-[3-(4-tertbutylphenyl)-2-methylprop-2-enylidene] malononitrile. This matrix was prepared as a 40 mg/mL solution in $CHCl_3$. The matrix solution (1 mg/mL) was applied to a stainless steel target and air dried. The samples were dissolved in THF and l microliter aliquots of this solution were applied onto the target area already bearing the matrix crystals and air dried. For the recording of the single-stage MS spectra, the quadrupole (rf-only mode) was set to pass ions from 200 to 2500 Th, and all ions were transmitted into the pusher region of the time-of-flight analyzer where they were mass analyzed with 1 s integration time.

Q-tOF (5600 ABSCIEX)—nanoESI-MS

Samples of fI.1 and fI.2 were diluted in 0.1% formic acid in acetonitrile, centrifuged at room temperature during 5 min at 13.000 RPM and the supernatants were infused directly in the Mass spectrometer (flow rate: 89 microliter/hour) using nano-esi source. The acquisition parameters were: ion source gas1:4; Curtain gas 15; ionspray Voltage floating 2.300, heater temperature 150° C.; Polarity: positive; ToF mass range: 100-2.000.

Ion Trap (HCT Ultra Brucker)—nanoESI-MS

Samples of fI.1 and fI.2 were diluted in 0.1% formic acid in acetonitrile, centrifuged at room temperature during 5 minutes at 13.000 RPM and the supernatants were infused directly in the Mass spectrometer (flow rate: 89 microliter/hour) using nano-esi source. The acquisition parameters were: capillary 1.900 Volt; Dry gas: 6 l/min; Dry temp: 250° C.; Polarity: positive; scan mode: Standard-enhanced; scan range: 100-2.000; Smart target 20.000; Max accu time: 200 ms.

Results

MALDI-ToF analyses of fI.1 and fI.2 showed that fI.1 and fI.2 comprise a number of compounds. In FIG. 2 the results of the Maldi Tof analysis of the fraction I.1 and the fraction I.2 are shown. Ten μl of each fraction was dried in presence of matrix.

Using Maldi-ToF data, Carotenoids and Quinones were observed in fI.1 (molecular ion indicated in brackets as M+H+ value): rhodovibrin (585.5), 1-hydroxy-spirilloxanthin (583.5), 3,4-didehydrorhodopin (587.5), chloroxanthin (557.5), bacteriopheophytin a (BPha; 883.5), rhodopsin (555.4), spirilloxanthin (597.4), 3,4-dihydrospirilloxanthin (599.5), phytyl derivative of bacteriopheophytin a (BPha (phytyl); 889.5), ubiquinol-10 (865.7), ubiquinone-9 (795.6), ubiquinone-10 (848.7) and rhodoquinone-10 (863.7). The same carotenoids and quinones were identified in the fI.1 extract when applying nano-ESI Q-ToF analysis.

Maldi-ToF data analysis with the fI.1 extract revealed, amongst others, peaks at the following m/z values (approximate relative intensity in brackets): 500.3 (1); 882.5 (1); 898.5 (4).

Maldi-ToF data analysis with the fI.2 extract revealed, amongst others, peaks at the following m/z values (approximate relative intensity in brackets): 500.3 (0); 882.5 (3); 898.5 (1).

Analysis of the fI.1 extract using Q-tOF (5600 ABSCIEX)—nanoESI-MS confirmed the presence of the above listed Carotenoids and Quinones present in fI.1. The NanoESI MS spectra are obtained for the fraction I.1 and the fraction I.2 with a triple tof mass spectrometer (ABSCIEX) using acetonitrile 99%, 1% HCOOC as organic solvent.

In the Q-tOF (5600 ABSCIEX)—nanoESI-MS spectrum for fI.1 amongst others, peaks were revealed at the following m/z values (approximate relative intensity in brackets): 647.6 (2.5); 651.6 (3.3); 881.5 (2); 927.5 (1).

In the Q-tOF (5600 ABSCIEX)—nanoESI-MS spectrum for fI.2 amongst others, peaks were revealed at the following m/z values (approximate relative intensity in brackets): 647.6 (2-3); 651.6 (16); 881.5 (5); 927.5 (1).

In the Ion Trap (HCT Ultra Brucker)—nanoESI-MS spectrum for fI.1 amongst others, peaks with relative high intensities were revealed at the following m/z values 652.3; 686.4; 690.6; 752.7; 769.3; 881.9; 897.8; 913.8; 927.7. NanoESI MS spectra are obtained for the fraction I.1 and the fraction I.2 with an IonTrap mass spectrometer (Bruker) using 1% HCOOC in acetonitrile.

The petroleum ether extract fI.1 of *Rhodospirillum rubrum* comprised compounds with a molecular weight of at least 2100 Da giving rise to peaks having an m/z value of 752.7 and 769.3 in a nanoESI-MS spectrum obtainable with the IonTrap nanoESI-MS high-resolution triple time-of-flight mass spectrometer (Bruker), said peaks with an m/z value of 752.7 and 769.3 having an intensity in the nanoESI-MS spectrum that is about five times the intensity of two further peaks in the nanoESI-MS spectrum having an m/z value of 665.8 and 883.6.

In the Ion Trap (HCT Ultra Brucker)—nanoESI-MS spectrum for fI.2 amongst others, peaks with relative high intensities were revealed at the following m/z values 665.8; 883.6; 899.8; 915.6.

The petroleum ether extract fI.2 of *Rhodospirillum rubrum* comprised compounds giving rise to peaks having an m/z value of 665.8 and 883.6 in a nanoESI-MS spectrum obtainable with the IonTrap nanoESI-MS high-resolution triple time-of-flight mass spectrometer (Bruker), said peaks with an m/z value of 665.8 and 883.6 having an intensity in the nanoESI-MS spectrum that is at least five times the intensity of two further peaks in the nanoESI-MS spectrum having an m/z value of 752.7 and 769.3.

Mice Test—Effect of fI.1, fI.2 and Fill on Plasma Cholesterol Level

The mice test for testing the influence of a diet comprising fI.1 or fI.2 or fill on plasma cholesterol level was performed at SCK·CEN animalarium (BE) following 2 weeks acclimation of 40 C57BL/6 male mice. After initial weighing of the food and the mice, they were placed in individual ventilated cage. Food consumption was checked every day and hydrogel weighed every 2 days. Based on previously performed preliminary palatability tests, the bacterial extracts were resuspended in sunflower oil, and 5% regular sugar was added to the chow (Cafetaria-diet) to ensure high palatability.

The first week, the first group of mice received the Cafetaria Diet+sunflower oil replacing *R. rubrum* extract fI.1 or fI.2 or fill ad libitum while the second group of mice received the Cafetaria Diet+the control diet replacing *R. rubrum* extract fI.1 or fI.2 or fill ad libitum.

The second week, the control group continued on the same diet while the three experimental groups received the Cafetaria Diet+10% of either the fI.1 extract or the fI.2 extract or the fill extract in sunflower oil. Thus, one group of mice was fed with feed comprising the fI.1 petroleum ether extract of *Rhodospirillum rubrum*, a second group of mice was fed with feed comprising the fI.2 extract of *Rhodospirillum rubrum*, a third group of mice was fed with feed comprising the fill extract of *Rhodospirillum rubrum*, a fourth group of mice, the control group, was fed feed without any of the extracts of *Rhodospirillum rubrum*.

Effects of feeding control feed or feed comprising either fI.1 or fI.2 or fill on cholesterol levels in plasma is detailed below.

End of Mice Test

After 2 weeks of testing, the mice where weighted and euthanized using intraperitoneal pentobarbital injection prior to dissection. Whole-blood was removed in EDTA-tubes, centrifuged to obtain plasma and placed at 4° C. for further analysis.

Mice Weight

After week 1 and week 2, no differences between the groups were detected.

Blood Analysis

Total Cholesterol, HDL and LDL Fractions

FIG. 1 shows the results of the cholesterol-, HDL- and LDL analysis.

Extract I.1 (which is Fraction I.1, fI.1) has a significant effect on the plasma LDL-cholesterol fraction since it decreased it for more than 40%, i.e. about 46%, compared to the control group ($p<0.001$) while the total cholesterol stayed essentially unchanged. See FIG. 1. Furthermore, also the HDL-cholesterol level in the mice group that were fed the fI.1 fraction, stayed essentially unaltered after the experimental period. Total cholesterol in plasma was 4,39 µg/µl for the fI.1 group of mice compared to 4,46 µg/µl for the control group, HDL-cholesterol was 2,93 µg/µl for the fI.1 group and 2,72 µg/µl for the control group, and LDL-cholesterol was 0,36 µg/µl for the fI.1 group ($p<0.001$) and 0,67 µg/µl for the control group, respectively.

Extract I.2 (which is Fraction I.1, fI.2), however, did not have a significant effect on any of the cholesterol levels when total cholesterol, HDL-cholesterol and LDL-cholesterol levels were concerned. See FIG. 1. Total cholesterol in plasma was 4,45 µg/µl for the fI.2 group of mice compared to 4,46 µg/µl for the control group, HDL-cholesterol was 3,00 µg/µl for the fI.2 group and 2,72 µg/µl for the control group, and LDL-cholesterol was 0,60 µg/µl for the fI.2 group ($p<0.001$) and 0,67 µg/µl for the control group, respectively.

Extract III (which is Fraction III, fill), similar to Extract I.1, also did not have a significant effect on of the cholesterol levels when total cholesterol, HDL-cholesterol and LDL-cholesterol levels were concerned. That is to say, total cholesterol in plasma remained unaltered at 4,46 µg/µl for the fill group of mice compared to the control group, HDL-cholesterol was 2,93 µg/µl for the fill group and 2,72 µg/µl for the control group, and LDL-cholesterol was 0,60 µg/µl for the fill group and 0,67 µg/µl for the control group, respectively.

From this mice test using *R. rubrum* S1H extracts fI.1 and fI.2 and fill, it is obvious that the petroleum ether extract fI.1 has a beneficial effect on lowering LDL-cholesterol level to a large extent, while at the same time keeping the HDL-cholesterol level essentially unaltered when the extract is administered orally. The mice test using *R. rubrum* S1H extract fI.2 or extract fill revealed that the compounds in these extracts do not significantly influence total cholesterol, HDL-cholesterol and LDL-cholesterol levels when the extracts are administered orally.

REFERENCES

D. E. Minnikin, A. G. O'Donnell, M. Goodfellow, G. Alderson, M. Athalye, A. Schaal and J. H. Parlett, "An integrated procedure for the extraction of bacterial isoprenoid quinones and polar lipids", *Journal of Microbiological Methods* 2 (1984) pp. 233-241 (Elsevier).

Segers, L. and Verstraete, W., 1983, Conversion of organic acids to H$_2$ by Rhodospirillaceae grown with glutamate or dinitrogen as nitrogen source. Biotechnol. Bioeng. 1983; 25: 2843-2853.

William W. Parson and Harry Rudney, "The Biosynthesis of Ubiquinone and Rhodoquinone from p-Hydroxybenzoate and n-Hydroxybenzaldehyde in *Rhodospirillum rubrum*", The Journal of Biological Chemistry, Vol. 240, No. 4, April 1965, pp. 1855-1863.

The invention claimed is:

1. An extract of *Rhodospirillum rubrum* that is obtained by extracting *R. rubrum* with a solvent mixture of petroleum ether and methanol containing sodium chloride, wherein the petroleum ether has boiling point between 60° C. and 80° C. wherein the *R. rubrum* is extracted for a period of time between 10 minutes and 48 hours at a temperature between 8° C. and 37° C., while mixing the *R. rubrum* cells with the solvent mixture, and wherein the ratio of petroleum ether to methanol comprising sodium chloride in a solvent mixture is between 10:1 and 1:10.

2. The petroleum ether extract of *Rhodospirillum rubrum* according to claim 1, wherein the extract is obtained by extraction for between 20 minutes and 24 hours, at between 10° C. and 30° C.

3. The petroleum ether extract of *Rhodospirillum rubrum* according to claim 1, wherein the extract is obtained upon centrifugation for between about ten minutes and 60 minutes, at between 15° C. and 25° C., after incubation of the *Rhodospirillum rubrum* cells in the solvent mixture.

4. The petroleum ether extract of *Rhodospirillum rubrum* according to claim 1, wherein the ratio of petroleum ether to methanol comprising sodium chloride in the solvent mixture is between 8:1 and 1:8.

5. The petroleum ether extract of *Rhodospirillum rubrum* according to claim 1, wherein the extract is obtained by extraction for between 1 hour and 3 hours at a temperature of between 15° C. and 25° C., and wherein the ratio of petroleum ether to methanol containing sodium chloride in the solvent mixture is 1:1.

6. The petroleum ether extract of *Rhodospirillum rubrum* according to claim 1, wherein the amount of sodium chloride in the methanol in the solvent mixture is between 0.02% and 0.04% by weight.

7. The petroleum ether extract of *Rhodospirillum rubrum* according to claim 1, wherein said extract comprises one or more carotenoids and/or one or more quinones.

8. The petroleum ether extract of *Rhodospirillum rubrum* according to claim 7, wherein said extract comprises one or more carotenoids selected from the group consisting of rhodovibrin, 1-hydroxy-spirilloxanthin, 3,4-didehydrorhodopin, chloroxanthin, bacteriopheophytin a, rhodopin, spirilloxanthin, 3,4-dihydrospirilloxanthin and phytyl derivative of bacteriopheophytin a, and/or one or more quinones selected from the group consisting of ubiquinol-10, ubiquinone-9, ubiquinone-10 and rhodoquinone-10.

9. The petroleum ether extract of *Rhodospirillum rubrum* according to claim 8, wherein said extract comprises rhodovibrin, 1-hydroxy-spirilloxanthin, 3,4-didehydrorhodopin, chloroxanthin, bacteriopheophytin a, rhodopin, spirilloxanthin, 3,4-dihydrospirilloxanthin, phytyl derivative of bacteriopheophytin a, ubiquinol-10, ubiquinone-9, ubiquinone-10 and rhodoquinone-10.

10. The petroleum ether extract of *Rhodospirillum rubrum* ccording to claim 1, for use as a medicament.

11. The petroleum ether extract of *Rhodospirillum rubrum* according to claim 1, for use in the lowering of LDL-cholesterol in blood plasma of a subject.

12. The petroleum ether extract of *Rhodospirillum rubrum* according to claim 1, for use in a method for the lowering of LDL-cholesterol in blood plasma of a subject.

13. The petroleum ether extract of *Rhodospirillum rubrum* according to claim 1, for use in the lowering of LDL-cholesterol in blood plasma of a subject or for use in a method for the lowering of LDL-cholesterol in blood plasma of a subject, wherein the subject surfers from or has an increased risk for any one or more of cardiovascular disease, atherosclerosis, dyslipidemia, arteriosclerosis, hypercholesterolemia, familial hypercholesterolemia, hyperlipidemia, an LDL plasma level of at least 70 mg/dL, a total cholesterol level of at least 200 mg/dL, an Lp(a) level of at least 14 mg/dL, inflammation, inflammatory disease, ischemia, or infection.

14. The petroleum ether extract of *Rhodospirillum rubrum* according to claim 1, wherein the extract is administered orally.

15. A food supplement with LDL-cholesterol lowering properties, comprising the petroleum ether extract of *Rhodospirillum rubrum* according to claim 1.

16. A foodstuff comprising the food supplement according to claim 15.

17. A method for the production of the petroleum ether extract of *Rhodospirillum rubrum* of claim 1, comprising the steps of:
  a) providing *Rhodospirillum rubrum* cells
  b) providing a biphasic mixture having about a 1:1 ratio by volume of petroleum ether that has a boiling point between 60° C. and 80° C. and methanol that comprises about 0.03% by weight of sodium chloride;
  c) mixing the cells of step a) with the biphasic mixture of step b) for about 1 to 3 hours at a temperature between 15° C. and 25° C.;
  d) separating the petroleum ether phase from the methanol phase of the biphasic mixture; and
  e) isolating the petroleum ether phase thereby, obtaining the petroleum ether extract of *Rhodospirillum rubrum*.

* * * * *